United States Patent [19]

Geysen

[11] Patent Number: 5,789,577
[45] Date of Patent: Aug. 4, 1998

[54] METHOD FOR THE CONTROLLED SYNTHESIS OF POLYNUCLEOTIDE MIXTURES WHICH ENCODE DESIRED MIXTURES OF PEPTIDES

[75] Inventor: H. Mario Geysen, Chapel Hill, N.C.

[73] Assignee: Chiron Corporation, Emeryville, Calif.

[21] Appl. No.: 760,919

[22] Filed: Dec. 6, 1996

Related U.S. Application Data

[63] Continuation of Ser. No. 366,662, Dec. 30, 1994, abandoned.
[51] Int. Cl.$^6$ .............................. C07H 1/62; C07H 21/00; C12H 15/00; C12H 15/10
[52] U.S. Cl. ...................... 536/25.31; 536/25.3; 435/6; 935/78; 935/79
[58] Field of Search ......................... 536/25.3, 25.31; 435/6; 935/78, 79

[56] References Cited

U.S. PATENT DOCUMENTS

| | | | |
|---|---|---|---|
| 5,010,175 | 4/1991 | Rutter et al. | 530/334 |
| 5,223,409 | 6/1993 | Ladner et al. | 435/69.7 |
| 5,264,563 | 11/1993 | Huse | 536/25.3 |

FOREIGN PATENT DOCUMENTS

| | | |
|---|---|---|
| WO 90/09395 | 8/1990 | WIPO. |
| WO 91/05058 | 4/1991 | WIPO. |
| WO 91/19818 | 12/1991 | WIPO. |
| WO 92/02536 | 2/1992 | WIPO. |
| WO 92/06176 | 4/1992 | WIPO. |
| WO 93/21203 | 10/1993 | WIPO. |
| WO 94/06451 | 3/1994 | WIPO. |

OTHER PUBLICATIONS

Virnekäs, B., et al., "Trinucleotide phosphoramidites: ideal reagents for the synthesis of mixed oligonucleotides for random mutagenesis," *Nucleic Acids Research*, 1994, 22(25):5600–5607.
Matteucci et al., "Synthesis of Deoxyoligonucleotides on a Polymer Support," *J. Am. Chem. Soc.* 103:3185–3191, 1981.
Geysen et al., "Strategies for epitope analysis using peptide synthesis," *J. Immunol. Meth.* 102:259–274, 1987.
Furka et al., 14th Int'l. Congress of Biochemistry, vol. 5, abstract FR:013, 1988.
Furka et al., "Computer Made Elechophoretic Peptide Maps," 2nd International Conference on Biochemical Separations, pp. 35, 38–42, 1988.
Furka et al., "More Peptides by Less Labor", Xth International Symposium on Medicinal Chemistry, Abstracts (1988).
Scott et al., "Searching for Peptide Ligands with an Epitope Library," *Science* 249:386–390, 1990.
Devlin et al., "Random Peptide Libraries: A Source of Specific Protein Binding Molecules," *Science* 249:404–406, 1990.
Furka et al., "General method for rapid synthesis of multicomponent peptide mixtures," *Int. J. Peptide Research* 37:487–493, 1991.
Hanvey et al., "Antisense and Antigene Properties of Peptide Nucleic Acids," *Science* 258:1481–1485, 1992.
Zuckerman et al., "Discovery of Nanomolar Ligands for 7–Transmembrane G–Protein–Coupled Receptors from a Diverse N–(Substituted)glycine Peptoid Library," *J. Med. Chem.* 37:2678–2685, 1994.

*Primary Examiner*—Gary L. Kunz
*Attorney, Agent, or Firm*—Bret Field; Kenneth Goldman; Robert P. Blackburn

[57] ABSTRACT

A method to obtain selected individual polynucleotides or mixtures thereof each of which encodes a peptide and at least one polynucleotide of the mixture encodes a peptide having a target property. The polynucleotides of the invention present in the mixture in detectable, retrievable, and clonable amounts are expressed in a host organism for screening for the target activity. The invention features the ability to synthesize controlled random polynucleotides to produce a predetermined mixture of polynucleotides and to avoid synthesis of a stop codon by adjusting the proportions into which the synthesis pool is subdivided and by adjusting the proportions of activated nucleotides added at each coupling step. A polynucleotide encoding a peptide having a target property can be selected and sequenced to deduce the amino acid sequence of the peptide.

38 Claims, No Drawings

METHOD FOR THE CONTROLLED SYNTHESIS OF POLYNUCLEOTIDE MIXTURES WHICH ENCODE DESIRED MIXTURES OF PEPTIDES

This is a continuation of application Ser. No. 08/366,662, filed Dec. 30, 1994, now abandoned.

FIELD OF THE INVENTION

The invention relates to methods of synthesis to obtain desired mixtures of polynucleotides. More particularly, the invention relates to methods for preparing controlled random mixtures of polynucleotides having codon sequences which encode desired mixtures of peptides.

BACKGROUND OF THE INVENTION

The concept of synthesizing every possible variation of small amino acid sequences has been addressed. Such peptides can be screened for biologically active peptides useful in the treatment or diagnosis of human diseases.

Although the synthesis of a particular peptide may be routine, it is necessarily laborious. This presents a large practical problem in a situation where it is not previously known which of a multiplicity of peptides is, in fact, the preparation desired. While it is theoretically possible to synthesize all possible candidates and test them with whatever assay is relevant (immunoreactivity with a specific antibody, interaction with a specific receptor, particular biological activity, etc.), to do so using the foregoing method would be comparable to the generation of the proverbial Shakespeare play by the infinite number of monkeys with their infinite number of typewriters. In general, the search for suitable peptides for a particular purpose by synthesis of individual peptides has been conducted only in cases where there is some prior knowledge of the most probable successful sequence. Therefore, methods to systematize the synthesis of a multiplicity of peptides for testing in assay systems would have great benefits in efficiency and economy, and permit extrapolation to cases where nothing is known about the desired sequence.

H. M. Geysen et al. (*J Immunol Meth* (1987) 102:259) devised an approach in which synthetic peptides were made by coupling an amino acid at a particular position from a mixture of amino acids. This approach provides all combinations of amino acids, but mixtures of peptides longer than approximately 15 residues will have a significant amount of undesired, shorter peptides as contaminants. Furthermore, because of this limitation, it is not possible to present the test peptide to the system of interest in any particular secondary structure, e.g., as an alpha-helix. This is because a length of polypeptide needs at least 20 or 30 residues before a particular secondary structure becomes dominant.

An alternative approach was suggested by Scott and Smith (Scott, J. K. and Smith, G. P., *Science* (1990) 249:386–390). It was suggested that the peptides could be encoded as part of a gene encoding a surface protein present at the tip of a filamentous bacteriophage. Expression of this surface protein containing the internally fused random peptide would overcome the limitation of peptide length associated with chemical peptide syntheses. Furthermore, using the method of Scott and Smith, the random peptide could be associated with additional amino acid sequences before and after the random section to provide a context within the whole fusion protein such that a particular secondary structure is achieved by the random peptide for presentation to a test system. This method also facilitates amplification of selected peptides (e.g., by propagating the bacteriophage after selection), and sequencing (e.g., by sequencing the nucleic acid insert in the amplified phage).

Scott and Smith proposed that a codon for which a random amino acid was to be synthesized would be prepared by coupling the first and second bases of each triplet from a mixture of A, C, G, and T. The last base would be coupled from a mixture of G and T under conditions allowing each base to be coupled with equal efficiency.

However, the strategy proposed by Scott and Smith has limitations. Firstly, it ensures that the "stop" codon [TAG] will appear in the mixture. Thus, if a "random" hexapeptide were required, more than 17% of the codons generated would have at least one stop codon. Since the last position of the codon triplet is limited to one of two nucleotides (G and T), it is possible to synthesize 32 codons, one of which is the stop codon having G in the final position (TAG). Thus, for each position one of 31 amino acid codons or one stop codon may be synthesized making the probability of synthesizing an amino acid codon for each triplet, 31/32 or 96.9%. However, for a hexapeptide, for example, the probability of synthesizing a six-codon polynucleotide containing no stop codon is reduced to 82.7% ($(96.7\%)^6$) Thus, approximately 17% of the six codon polynucleotides synthesized by this method will have at least one stop codon and would not be fully expressed.

The amino acids are encoded by different numbers of codons. The redundancy of the genetic code means that in using this strategy, a total of $1.07 \times 10^9$ ($32^6$, where 32 is the number of possible codons) different codon sequences need to be made to encode the $6.4 \times 10^7$ possible hexapeptides ($20^6$, where 20 is the number of naturally occurring amino acids). Further, under the system outlined above, the amino acid methionine will be encoded only by the triplet [ATG]; however, serine will be encoded by three codons, [TCT], [TCG] and [AGT]. Thus, the possibility of obtaining serine at a given triplet position is three times greater than that of methionine thus creating a statistical bias in the synthesis of random peptides toward amino acids encoded by multiple codons.

SUMMARY OF THE INVENTION

The invention involves a method of synthesizing mixtures of polynucleotides which encode and can be made to express mixtures of peptides wherein the peptides are present in the mixtures in any desired relative amounts. The method is carried out by 1) splitting a mixture of prepared resins into separate pools (subamounts); 2) synthesizing, on the resins, codons (i.e., polynucleotide triplets representing the twenty naturally occurring amino acids) by reacting nucleotides in sequential reactions to obtain codon sequences; and 3) recombining subamounts of codon sequences at which time the codons for each of the twenty amino acids will be present in the desired relative amounts, e.g., equal amounts. The steps are repeated to increase the length of the codon sequences by a single codon per iteration and thereby produce codon sequences which encode longer peptides of controlled random sequence.

For example, to avoid synthesis of stop codons and to provide an equal probability of coding for each amino acid at a given position, the solid phase oligonucleotide synthesis resin is divided into 20 subamounts and a codon is synthesized for each random amino acid (specifically avoiding the synthesis of a stop codon). The subamounts are then mixed and reapportioned into new subamounts in preparation for the next round of synthesis. In so doing, each subamount has the codon for a particular amino acid covalently attached to the resin.

In practice, dividing the resin into 20 subamounts is useful only for short polynucleotides (or longer sequences with only a few unknowns) encoding random peptides due to the need for large amounts of resin required to produce a library of all polynucleotides of a desired length. Using polynucleotides encoding a hexapeptide as an example, 20 possible codons at each of six positions produce a theoretical minimum of $(20)^6$ or $6.4 \times 10^7$ synthetic species. Thus, a minimum number of $6.4 \times 10^7$ resin particles are required on which to "build" a random hexapeptide-encoding polynucleotide mixture assuming that one resin bead is allocated on average for each synthetic species. Because the resin is thoroughly mixed between each coupling cycle, the polynucleotide on each individual resin bead will be randomly distributed among the subamounts approximately according to a Poisson distribution—an excellent approximation of the process. Using the Poisson distribution as a model to calculate the distribution of polynucleotides, approximately 37% of all the expected polynucleotides synthesized will be missing from this library (i.e., they have been effectively made on zero resin beads or they have effectively not been made). Thus, 23.5 million of the expected 64 million polynucleotides will be missing. On the other hand, some of the polynucleotides will be synthesized on more than one resin bead. Statistically, more than one million of the polynucleotides are made on four or more resin beads. Increasing the number of beads to an average of 100 resin beads per polynucleotide synthesized in the library provides that substantially every possible polynucleotide sequence for a particular library will be made on at least 50 resin beads and no polynucleotide will be made on 160 beads or more. The end result is that there will be a spread of concentrations of polynucleotides among the resin beads. For practical purposes, selecting 100 resin beads per peptide is sufficient to achieve a usable library in which every intended polynucleotide is synthesized and is present in the mixture in a detectable and clonable amount. This is also true if more than one polynucleotide is synthesized per resin bead as is the case in the present invention. Thus, in practice, at least two orders of magnitude excess resin is required for synthesis of detectable and clonable amounts of each species making the total amount of resin required $6.4 \times 10^9$ resin particles. At a typical volume of $5 \times 10^5$ resin particles per milliliter, a volume of $1.3 \times 10^4$ ml or 13 L of resin would be required; clearly an impractical situation.

An advantage of the present invention is that by dividing the support resin into relatively few subamounts (e.g., 4 or 5 subamounts), the required amount of resin is reduced. The minimum amount of resin required is the number of prepared support resin particles that can be divided by the smallest subamount as many times as there are repetitions of the cycle of dividing, coupling, and pooling of the subamounts to add a codon. Preferably, an amount of resin particles is used that is two orders of magnitude greater than the minimum amount of resin required.

A primary object of the invention is to provide a method of making a mixture of polynucleotides having a known composition and encoding a plurality of different peptides (preferably encoding at least one biologically active peptide with a target property) wherein each of the different polynucleotides is present in an amount sufficient for detection and cloning.

A feature of the invention is a method of preparing a mixture of polynucleotides having different nucleotide sequences, which mixture contains detectable, retrievable, and clonable amounts of each polynucleotide. The method involves the following steps of first dividing an amount of a prepared support resin into a plurality of subamounts of known proportions; next, coupling to one of the subamounts a first activated nucleotide from a mixture of at least one activated nucleotide, wherein the activated nucleotide in said mixture is present in a known proportion relative to the reactive sites on the resin and in a known proportion relative to other activated nucleotides that may be present in the coupling mixture. From this coupling step, a plurality of different resin-nucleotide reaction products are obtained and the coupling is carried out under conditions such that the coupling is driven to substantial completion. The 3' reactive site of the resin-nucleotide is deprotected following the coupling reaction to allow subsequent coupling reactions.

The next step is coupling to the subamount a second activated nucleotide from a mixture of at least one activated nucleotide, wherein each of the activated nucleotides is present in the mixture in a known proportion and a plurality of resin-nucleotide reaction products are obtained. The coupling is carried out under conditions that drive the coupling to substantial completion. Following coupling of a second nucleotide, the 3' reactive site of the resin-nucleotide is deprotected to allow subsequent coupling reactions.

The next step involves coupling to the subamount a third activated nucleotide from a mixture of at least one activated nucleotide, wherein each of the activated nucleotides is present in the mixture in a known proportion and a plurality of resin-nucleotide reaction products are obtained. The coupling is carried out under conditions that drive the coupling to substantial completion. Following coupling of a third nucleotide, the 3' reactive site of the resin-nucleotide is deprotected to allow subsequent coupling reactions or other processing of the resin-nucleotide mixture well known to those of ordinary skill in the relevant art of solid phase polynucleotide synthesis.

To each of the remaining subamounts is coupled activated nucleotides from mixtures of activated nucleotides as in steps described above involving the coupling of a first, a second and a third activated nucleotide to obtain a mixture of resin-nucleotides.

The reaction products of the couplings to each of the subamounts are combined to produce a controlled random mixture of resin-polynucleotide reaction products. Using the controlled random mixtures of the combined subamounts and repeating in order the dividing; coupling of the first, second, and third activated nucleotides to each of the subamounts; and combining steps until a controlled random mixture of polynucleotides is obtained, wherein each of the polynucleotides encodes the desired number of amino acids. The composition of the random mixture of resin-nucleotide reaction products includes substantially equimolar amounts of each naturally-occurring amino acid at at least one of the codon positions of said resin-polynucleotide products. Another object is to detect, clone and express the synthesized codon sequences so as to obtain a mixture of peptides with the peptides being present in any desired relative amounts.

Another object of the invention is to use RNA or DNA synthesized by the method of the invention without expressing the RNA or DNA as a peptide. For example, RNA can be used to hybridize to RNA or DNA of interest; DNA synthesized by the method of the invention can be used as probes, as primers, and as sequences useful in optimizing promoters when operably linked to a gene.

An advantage of the invention is that the coupling reactions in the individual pools can be driven to completion by adjusting reaction conditions and adding large excesses of each of the activated nucleotides added to the pools in relative amounts adjusted to account for differences in reaction rate.

A feature of the invention is that the synthesis protocol is designed such that codon synthesis is controlled and a stop codon can be introduced when desired but may also be avoided if desired.

Another feature of the invention is that for each synthetic iteration, a different codon synthesis scheme can be used. The number of subamounts may vary from iteration to iteration allowing for maximum flexibility in the design of the polynucleotide mixture.

Another feature of the invention is that it allows for avoidance of sequence dependent difficulties observed in polypeptide synthesis such as hairpin formation in amino acid sequences.

Another object of the invention is to provide a method which allows for a specific synthetic protocol for producing a composition which includes a complex mixture of polynucleotides (the composition of the mixture being known based on the protocol) thus eliminating the need for characterization of the mixture after synthesis.

Another feature of the invention is the reduction in the amount of support resin necessary to produce a library of controlled random polynucleotides relative to the amount of support resin necessary to produce the same library by previous methods.

Yet another object of the present invention is to provide a method for producing a mixture of polynucleotides encoding peptides which mixture will encode a peptide having a desired target property.

Another feature of the present invention is that each of the polynucleotides in the mixture of polynucleotides (having a given nucleotide sequence, encoding random peptides and being produced according to the disclosed process) are each present in detectable and clonable amounts.

A feature of the invention is that at each controlled randomized codon of the polynucleotides each amino acid is encoded in controllable amounts such as in equimolar amounts.

Another feature of the invention is that the product of the method of the invention can be a polynucleotide having a nonribophosphate backbone. Alternative backbone structures include but are not limited to peptide backbones having purine and/or pyrimidine bases as side chains; and peptoid backbones (Hanvey, J. C. et al. (1992) *Science* 258:1481–1485; Zuckerman, R. et al. PCT/US/93/09117 filed Sep. 24, 1993 and U.S. patent application Ser. No. 08/277,228 filed Jul. 18, 1994, each herein incorporated by reference specifically for the purpose of showing that purine and pyrimidine side chains can be added to a nonribophosphate backbone) having purine and/or pyrimidine bases as side chains.

An advantage of the present invention is that it allows for the production of an extremely large number of different polynucleotides encoding random peptides in a polynucleotide mixture which polynucleotides can then be cloned, expressed in vivo or in vitro and screened for the presence of peptides having a particular target property.

Another advantage of the present invention is that extremely large numbers of peptides can be produced utilizing few processing steps to produce the polynucleotides encoding them.

Another advantage of the present invention is the ability to more quickly and efficiently produce larger numbers of longer peptides than is possible by conventional chemical peptide synthesis.

These and other objects, advantages and features of the present invention will become apparent to those persons of ordinary skill in the art upon reading the details of the synthesis and usage as more fully set forth below.

DETAILED DESCRIPTION

Before the present method of making a mixture of polynucleotides encoding peptides and the process for determining the composition of a complex mixture of polynucleotides are described, it is to be understood that this invention is not limited to the particular polynucleotides, amino acids, resins, peptides or processes described as such reactants and processes may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to a "polynucleotide" or "peptide" includes a large number of polynucleotides of the same sequence or peptides of the same sequence and reference to "the process" or "the step" includes alternative processes and steps of the general type described herein and so forth.

DEFINITIONS

As used in connection with the present invention, "prepared resin" shall mean a solid support material having on its surface acceptor groups which react with and form a covalent bond with activated nucleotides. Non-limiting examples of such solid support materials include a variety of support resins and connectors to the support resins such as those which are photocleavable, DKP-forming linkers (DKP is diketopiperazine; see e.g., WO90/09395 incorporated herein by reference), TFA cleavable, HF cleavable, fluoride ion cleavable, reductively cleavable, and base-labile linkers.

The acceptor groups may include covalently attached compounds such as nucleotides or leader nucleotide sequences to which may be coupled activated nucleotides by the method of the invention. Further, the term "nucleotide derivatized resin" shall mean a mixture of acceptor polynucleotides wherein the 5' nucleotide terminus is covalently attached to the resin and wherein the 3' nucleotide terminus is activated for coupling to a next nucleotide at its 5' reactive position. Accordingly, such "nucleotide resins" or "prepared resins" are generally classified as being "acceptors" meaning that additional nucleotides can be added at their 3' terminus. Further, unless described as a "single" compound, disclosed compositions are mixtures of polynucleotides or resins i.e. heterogeneous groups of compounds produced from single compounds by polymerization. The heterogeneous group or mixture will contain a statistical mixture of compounds i.e., a range of different compounds over a range of proportional amounts.

The term "activated nucleotide" shall mean a nucleotide which reacts with and covalently binds to a resin or nucleotide-derivatized resin under conditions such that the 5' hydroxyl, but not the 3' hydroxyl, group is available for covalent bond formation with the acceptor resin. An activated nucleotide is protected by a protecting group (such as dimethoxytrityl, DMT) at the 3' hydroxyl to avoid multiple coupling reactions in a given single step. Accordingly, terms such as "acceptor" and "acceptor resin" describe an activated compound which will react with and bind to the 3' hydroxyl group of a nucleotide deprotected at the 3' hydroxyl group, whereas terms such as "nucleotide" and "activated nucleotide" describe the activation of the 5' hydroxyl group of the nucleotide and indicate that such nucleotides will react with and form a covalent bond with the reactive group of the resin. It should be noted that 3' to 5' synthesis (i.e., reverse synthesis) is also possible by the method of the invention, thus changing the definition of "acceptor" and "activated nucleotide." Activating and protecting groups as well as protection and deprotection reactions useful in carrying out solid phase synthesis are well known to those of ordinary skill in the art of solid phase nucleotide synthesis.

"Protecting group" means any group capable of preventing the atom to which it is attached, usually oxygen or nitrogen, from participating in an undesired reaction or bonding, usually in a synthesis reaction. Such groups and their preparation and introduction are conventional in the art and include salts, esters and the like.

A "purine or pyrimidine base" includes the natural nucleoside bases, such as A, T, G, C or U, and also derivatives thereof including those purines and pyrimidines substituted by one or more of alkyl, caboxyalkyl, amino, hydroxyl, halogen (i.e. fluoro, chloro, bromo, or iodo), thiol, or alkylthiol wherein the alkyl group contains from 1 to about 6 carbon atoms. Non-limiting examples of purines and pyrimidines include 2,6-diaminopurine, 5-fluorouracil, xanthine, hypoxanthine, 8-bromoguanine, 8-chloroguanine, 8-aminoguanine, 8-hydroxyguanine, 8-methylguanine, 8-thioguanine, 2-aminopurine, 5-ethylcytosine, 5-methylcyosine, 5-bromouracil, 5-ethyluracil, 5-iodouracil, 5-propyluracil, 2-methyladenine, methylthioadenine, N,N-diemethyladenine, 8-bromoadenine, 8-hydroxyadenine, 6-hydroxyaminopurine, 6-thiopurine, 4-(6-aminohexyl/ cytosine) and the like.

The invention can include the use of conventional solid-phase methods of nucleotide syntheses which methods are illustrated in this disclosure using the chemistries by which nucleotides are added to the 3'-end of the lengthening polynucleotide. It will be obvious to those of ordinary skill in the art that the invention can be easily extended to other methods of synthesis (including liquid-phase methods) and to other chemistries. For instance, to use the more common method by which bases are added to the 5'-end of the lengthening polynucleotide, the bases would be coupled in reverse order from that given in the examples below. Furthermore, the examples use the "Universal Genetic Code". From reading this disclosure it will also be apparent that the invention can be applied to variants of the genetic code.

By "detectable, retrievable, and clonable amount" of a polynucleotide sequence is meant an amount that can be observed, collected, and manipulated by conventional chemical and molecular biological methods well known to those of ordinary skill in the relevant arts. An exemplary method includes detection by PCR (polymerase chain reaction) amplification.

"Target" characteristic or property refers to that biological or physical property desired to be exhibited by the peptide or family of peptides, such as specific binding characteristics, contractile activity, behavior as a substrate, activity as a gene regulator, etc.

The solid phase synthesis methodology described herein can be applied to solution phase synthesis, wherein the acceptor nucleotides or polynucleotides are supplied as a mixture for reaction with an appropriate mixture of activated nucleotides. Either or both mixtures are concentration-adjusted to account for rate constant differentials.

By "coupling" is meant the reaction of an acceptor molecule and a donor molecule where the acceptor molecule in the examples below is the 5' nucleotide of the growing sequence and the donor molecule is the activated nucleotide which becomes the 3' nucleotide of the growing chain following reaction. This 3' nucleotide becomes the 5' nucleotide in the next chain-lengthening reaction. The activated nucleotide or nucleotide mixture is added in an amount and under conditions so as to provide a substantially complete coupling reaction with all of the nucleotide- or polynucleotide derivatized resins in each of the subamounts. Thereafter, the polynucleotides in each of the separated subamounts are combined in order to provide a mixture of polynucleotides which encode substantially equimolar amounts of each amino acid in the last-synthesized codon. The coupling reaction can be monitored for completion using techniques known to those of ordinary skill in the art.

By "substantial completion" is meant reaction of 98% or more and preferably all available reactive 5' acceptor molecules capable of reacting under conditions of excess activated nucleotide in a given synthetic step.

By "substantially equimolar" is meant molar amounts of resin, nucleotide, or other agent which is present in molar amounts that are similar (within 50%, preferably within 20%, more preferably within 10% of each other in molar amounts) within the practice of the art by one of ordinary skill.

By "naturally occurring amino acid" is meant one of the 20 L-form amino acids synthesized naturally by a given host or in vitro reaction in which the product polynucleotide is expressed. The schemes and examples disclosed herein use naturally occurring amino acids for the purpose of providing a guide to the ordinarily skilled artisan. The twenty naturally occurring amino acids are Phe, Leu Ser, Tyr, Cys, Trp, Pro, His, Gln, Arg, Ile, Met, Thr, Asn, Lys, Val, Ala, Asp, Glu, and Gly. Any amino acid derivative that is encoded by a given codon in a mutant host or in an in vitro expression system can be substituted if desired.

By "expression in vivo" or "expression in a host" is meant the transcription and translation of a random polynucleotide sequence synthesized by the method of the invention. Prior to expression, a complementary strand to each random polynucleotide is synthesized by molecular biological techniques well known in the art to produce double stranded DNA. This is followed by cloning of the double stranded random polynucleotide into an expression vector, and then introduced into a host organism capable of transcribing and translating the random polynucleotide sequence into a peptide also having a random amino acid sequence.

By "expression in vitro" is meant providing a random polynucleotide by the method of the invention followed by synthesis of a complementary strand for each polynucleotide to generate double stranded DNA. This is followed by expression of the random polynucleotide sequence by a standard in vitro expression system well known to those of ordinary skill in the art.

By "A, T, C, G, U" is meant adenine, thymine, cytosine, guanine, and uracil respectively, and the activated nucleotide derivatives thereof.

By "polynucleotide" or "oligonucleotide" is meant a chain of at least two nucleotides covalently attached at the 3' hydroxyl position of a first nucleotide and the 5' hydroxyl position of a second nucleotide. The term polynucleotide or oligonucleotide also encompass oligomers having a nonribophosphate backbone. Such nonribophosphate backbone structures include but are not limited to peptide or peptoid backbones (Zuckerman, R. N. et al., *J. Med. Chem.* 37:2678–2685) having purine and/or pyrimidine bases as side chains.

By "amber stop codon" is meant the codon TAG (UAG in the transcribed form) which is not transcribed but codes for transcriptional termination in bacteria. Certain bacterial mutants which produce an amino acid or amino acid derivative-charged TRNA can insert an amino acid or amino acid derivative at the amber codon thus increasing the variety of amino acids that may be inserted at a given position.

By "biological activity" or "target activity" is meant the ability of a product polynucleotide, peptide, or peptoid to bind to a desired protein (such as an antibody), peptide, nucleic acid to produce a desired activity.

MODES OF CARRYING OUT THE INVENTION

Synthetic oligonucleotides may be prepared by any convenient method known in the art, for example, the triester method of Matteucci et al, *J Am Chem Soc* (1981) 103:3185, or using commercially available automated oligonucleotide synthesizers. In general, it is presently preferred to synthesize oligonucleotides coupled to an appropriate resin or other solid support. The support is preferably provided in a finely divided or particulate form (small spherical beads) that may easily be divided and aliquoted.

A suitable quantity of support material is first prepared for coupling by methods known in the art. One may attach or synthesize a short leader nucleotide sequence, to provide, for example, a leader encoding a restriction enzyme recognition site to facilitate later ligation into a vector. The leader may also serve as a convenient hybridization site for a PCR (Polymerase Chain Reaction) primer, to enable facile amplification of the product polynucleotide. If desired, one may use a number of different leaders, to provide a means for distinguishing between different portions of the support particles and/or polynucleotides. The leader sequence may alternatively or additionally provide a cleavage site, to facilitate cleavage of the polynucleotides from the support particles by enzymatic or chemical means.

According to the invention, the prepared support is divided into either four or five portions, depending on the scheme selected. There are five schemes provided below each producing polynucleotides encoding codons representing a substantially equimolar mixture of amino acids at each controlled randomized position. One scheme includes a stop codon while the rest specifically avoid the synthesis of a stop codon. A method of preparing a mixture of nucleotides with different sequences of codons, having a known composition, and containing at least one polynucleotide encoding a peptide having a target property is disclosed. The method involves three essential steps as follow:

(1) a given amount of a mixture of prepared nucleotide- or polynucleotide-derivatized resins are divided into a number of pools (or subamounts; preferably twenty, more preferably four or five subamounts) with each pool (or subamount) containing a controlled amount (such as a substantially equal molar amount) of each resin or containing a varied molar amount of each resin where the molar ratios of subamounts is known and controlled;

(2) a single activated nucleotide from a mixture of nucleotides is coupled to each resin in each of the pools (or subamounts) created in step (1) and the coupling reaction is driven to completion to obtain a resin-nucleotide reaction product;

(3) a second single activated nucleotide from a mixture of nucleotides is coupled to each resin in each of the pools (or subamounts) created in step (1) and the coupling reaction is driven to completion to obtain a resin-nucleotide reaction product;

(4) a third single activated nucleotide from a mixture of nucleotides is coupled to each resin in each of the pools (or subamounts) created in step (1) and the coupling reaction is driven to completion to obtain a resin-nucleotide reaction product;

(5) the resin-nucleotide reaction product obtained in each of the pools (or subamounts) obtained in steps (2) through (4) are then mixed together to obtain a polynucleotide mixture of known composition (i.e., containing substantially equal molar amounts of each of the codons encoding the twenty naturally occurring amino acids at each codon position); and (6) Using the mixture obtained in step (5) as the starting material as per (1) above and repeating steps (2) through (5) until a random mixture of polynucleotides, each encoding the desired number of amino acids, is obtained.

Two important points should be made: (a) the steps (1) through (5) can be repeated any number of times to lengthen the polynucleotide chain, and (b) each codon of the lengthening polynucleotide is generated such that the sum of the codons at step (5) encodes each of the twenty amino acids in known amounts, e.g., in substantially equimolar amounts; or encodes a subset of the twenty amino acids as desired for each site.

Amounts of varied polynucleotides and mixtures can be used as acceptors independently with respect to the next activated nucleotide addition to create lengthened polynucleotide acceptors which can be remixed and divided. In that the method produces a large number of polynucleotides (each with a different sequence) in detectable and clonable amounts, the method is an extremely powerful tool for obtaining a large group of polynucleotides which can be cloned, expressed to obtain a mixture of peptides which mixture can be screened for a peptide having a desired target biological property.

Methods can be employed to detect the desired polynucleotide in the mixture and carry out analyses such as the determination of the nucleotide sequence by methods known to those of ordinary skill in the art. In steps (2) through (4), sufficient amounts of activated nucleotides are added so as to produce enough of the polynucleotide in each pool so that when the pools are combined in step (5) each of the polynucleotides in the resulting mixture will be present in that mixture in a detectable and clonable amount.

The invention permits a practical synthesis of a mixture of a multitude of polynucleotide sequences, in predictable and defined amounts (within statistically acceptable variation) for the intended purpose. In addition, the invention permits this mixture to be cloned, expressed, and screened or selected for the desired peptide, individually or as groups. The invention also permits the determination of sequences of these selected polynucleotides since they can be individually synthesized in large amounts if desired. Because mixtures of many polynucleotides are used, prejudicial assumptions about the nature of the sequences required for the target biological activity is circumvented. However, if information about a peptide is known, such as the amino acid residue at a given position in the chain, that information can be readily employed in the method of the invention by synthesizing the correct codon at the correct position in the polynucleotide that encodes the amino acid known to be at that position.

Thus, in one aspect, the invention is directed to a method of synthesizing a mixture of polynucleotides of defined composition encoding random peptides. The relative amounts of each codon of a polynucleotide in the mixture can be controlled by changing the molar ratio of each nucleotide in the mixture of activated nucleotides in steps (2), (3) and (4), above. The relative amount of each codon of a polynucleotide in the mixture can also be controlled by changing the molar ratios of starting resin in each of the pools or subamounts in step (1) or (6), above, or subsequent steps (11), (16), (21), etc.

The method of the present invention is carried out under conditions that drive all coupling reactions to completion making it irrelevant whether the acceptors have the same relative rates of reaction for reacting with all activated nucleotides. Differences in relative rate constants are not a factor effecting the composition of the mixture of polynucleotides obtained.

It should be noted that while the invention method of synthesis is most usually and practically conducted using solid-supported polynucleotides, there is no reason it cannot be employed for solution phase synthesis, wherein the acceptor nucleotide or polynucleotide is simply blocked at the 5' hydroxyl group.

In another aspect, the invention is directed to a method of selecting those components (individually or as families) of the mixture which have the desired "target" biological activity. Sequence information on these polynucleotides can also be obtained. Thus, the invention is also directed to a method of separating the desired polynucleotide from the original composition. This involves effecting differential behavior under conditions which result in physical separation of components, such as binding to a selective moiety (e.g., interaction of a leader sequence on the synthesized polynucleotide with a complementary sequence in a column for separation). Separation can be performed on the initial mixture or on the cloned species such that the vector containing the synthesized polynucleotide is isolated following expression in vivo or in vitro.

In another aspect, the invention is directed to a method of cloning the polynucleotide of the invention such that the polynucleotide is amplified for sequencing. The polynucleotides synthesized by the method of the invention may also be cloned into suitable cloning vectors for expression of the polynucleotide in a host (in vivo) or in vitro such that the desired mixture of random peptides is produced for testing of the desired "target" activity.

In addition to the foregoing aspects, various additional combinations thereof are useful.

PRODUCING A DESIRED POLYNUCLEOTIDE

In general, an ultimate goal of the invention is to provide a means to obtain one or a family of specific peptide sequences which have a "target" activity such as the ability to bind a specific receptor or enzyme, immunoreactivity with a particular antibody, and so forth. To achieve this end, the invention provides a means of synthesizing polynucleotides containing codons the sum of which represents the twenty naturally occurring amino acids (or a desired subset) in controlled amounts, preferably substantially equimolar amounts. The invention further provides that the amino acid sequence encoded by the polynucleotide is random. The invention most preferably involves the following aspects:

(a) preparation of a mixture of many polynucleotides putatively containing the codon sequence of a desired peptide;

(b) detection, retrieval, and/or cloning of a polynucleotide from the mixture for the expression of the encoded random peptides and selection for the desired characteristics; and (c) analysis of the polynucleotide encoding the selected peptide such that the nucleotide sequence is determined and the amino acid sequence of the selected peptide is deduced from the nucleotide sequence. Using this information, the polynucleotide or encoded selected peptide having the desired characteristics may be synthesized in quantity by methods well known to those of ordinary skill in the art.

The essence of the invention is in the preparation (a) which is carried out in steps (1) through (6) referred to above. Unless a mixture is produced containing detectable amounts of each of the different polynucleotides, no polynucleotide could be detected and without the detection, as stated above in (b), no analysis, as stated above in (c), can be carried out.

Since a complex mixture of polynucleotides is synthesized as the starting material for selection, it is not necessary to know the sequence of the biologically active product. The method is also applicable when preliminary assumptions about the desired polynucleotide sequence can reasonably be made. In fact, the ability to make valid assumptions about the nature of the desired sequence is an advantage the method of the invention. However, the advantages of the present invention over the prior art are further emphasized when less is known about the desired polynucleotide and ultimately about the desired peptide having the "target" biological activity.

Using for illustration only the twenty naturally occurring amino acids, a mixture of polynucleotides encoding a hexapeptide, for example, in which each amino acid is independently one of these amino acids will contain $(20)^6$ or $6.4 \times 10^7$ possible members, thus requiring the synthesis of $6.4 \times 10^7$ different polynucleotide sequences each encoding a hexapeptide, one of which hexapeptides has a biological activity (such as binding an epitope of a monoclonal antibody). A procedure for synthesizing such a mixture of hexapeptides is illustrated in Geysen, H. M., et al. (*J Immunol Meth* (1987) 102:259) using the process of pooling and subdividing a resin mixture to produce a peptide (such as a hexapeptide) sequence containing any one of the 20 natural amino acids at each site. In this method of synthesizing amino acid sequences, a pool of resin is divided into 20 portions, each of which portions is reacted to completion with a different amino acid. The pools are mixed and redivided into 20 portions for coupling of the next amino acid. These steps are repeated until a mixture of $20^6$ hexapeptides is produced. Advantages of the present invention in subdividing the resin into fewer portions and synthesizing polynucleotides rather than peptides has been described herein, supra.

The polynucleotide mixtures of the present invention, in order to be subjected to procedures for cloning and analysis of the desired members, must provide enough of each member to permit selection and analysis. Using the current requirement, imposed by limitations of available selection and analysis techniques, approximately 0.01 pmol of a single stranded polynucleotide (18mer in this example) is needed in order to PCR (polymerase chain reaction) amplify the polynucleotide to generate double stranded species from each polynucleotide and to increase the total amount for convenient cloning. Next the double stranded polynucleotide can be cloned and amplified in a host organism for expression of the encoded random peptide. Expression systems for in vivo amplification and expression include but are not limited to plasmid vector expression in *E. coli* or yeast well known to those of ordinary skill in the art. Expression of the double stranded polynucleotide (such as RNA) can be performed in vitro using in vitro expression systems well known to those of ordinary skill in the art such as rabbit reticulocyte translation systems (Promega, Inc., Madison, Wis.).

An advantage of the present invention is that polyribonucleotides can be synthesized for the preparation of random mixtures of RNA sequences to be used in screening for antisense RNA or for screening of RNA having ribozyme activity.

An important feature of the invention is the ability to synthesize a large number of different polynucleotides having codons representing each of the twenty naturally occurring amino acids in which the amino acids are represented in controllable relative amounts (such as substantially equimolar amounts). Multiple polynucleotide sequences are attached to each resin bead as a result of the process of reacting the resin bead with mixtures of nucleotides, dividing, and pooling the resin. The multiple polynucleotide sequences are randomly distributed over the resin material.

The method of the invention has the advantage of allowing the coupling of optional polynucleotide sequences at one or both ends of the sequences synthesized by the method of the invention. For example, the optional sequences can provide a restriction enzyme cleavage site when the sequence is made double stranded. The optional sequences can also provide sites for hybridization of primers for PCR amplification or can encode a separate, traceable peptide to be expressed along with the randomly synthesized peptide as a fusion peptide. Mixtures of sequences synthesized by the method of the invention and made double stranded by methods well known to those of ordinary skill in the art can be linked by blunt end ligation to further randomize the mixture and lengthen the polynucleotide sequences. Polynucleotide mixtures of the invention can also be cloned into known genes to randomize positions of known proteins for the purpose of optimizing or analyzing activities of particular protein domains (Ladner, et al. U.S. Pat. No. 5,223,409 issued Jun. 29, 1993, herein incorporated by reference to describe expression of recombinant proteins and display of the potential binding domain of the protein on the outer surface of a chosen bacterial cell, bacterial spore or phage).

The method of the invention provides the advantage of reducing the amount of resin necessary to synthesize large numbers of sequences by teaching division of the synthesis support or resin into relatively few subamounts (preferably four or five subamounts) and coupling activated nucleotides from mixtures of activated nucleotides in controlled molar ratios. The following schemes provide illustration of this advantage and are not to be construed as limiting the invention in any way.

EXAMPLES

The schemes and related examples presented below are provided as a guide to the practitioner of ordinary skill in the art, and are not to be construed as limiting the invention in any way. Each scheme and example begins with a solid support resin that is divided into known proportions, coupled with activated nucleotides in known proportions in three steps to form a new codon. The resin portions are recombined to provide a mixture of codons and the mixture is reapportioned for the next addition of a new codon. The dividing, coupling, and recombining are continued until a desired number of codons have been linked to the resin.

SCHEME 1

The synthesis support resin is divided into four unequal subamounts, having a molar ratio of 6:3:7:5. This ratio corresponds to the number of encoded amino acids present in each subamount at the end of a cycle of codon synthesis. To the first subamount (molar ratio 6) is coupled the nucleotide T; next is coupled a mixture of A, T, and G in substantially equimolar amounts; next is coupled a mixture of G and T or G and C in substantially equimolar amounts. This provides six codons: TAG, TAT, TTG, TTT, TGG, and TGT (or TAG, TAC, TTG, TTC, TGG, and TGC), which encode stop (amber), Tyr, Leu, Phe, Trp, and Cys, respectively, in substantially equal ratios.

To the second subamount (molar ratio 3) is coupled C; next is coupled a mixture of C and A having effectively half the molar ratio of C as A; next is coupled a mixture of T and G in substantially equimolar amounts. This provides four codons: CCT, CAT, CAG, and CCG, which encode Pro, His, Gln, and Pro, respectively. Although two codons encode Pro in this subamount, the ratio of Pro codons to the codons of each of the other two amino acids is 1:1 due to the reduced ratio of C to A in the synthetic mixture resulting in half the amount of each of CCT and CCG as CAT and CAG.

To the third subamount (molar ratio 7) is coupled A; next is coupled a mixture of A, C, G, and T in an effective molar ratio of 2:1:2:2, respectively; next is coupled a mixture of G and T in substantially equimolar amounts. This provides eight codons: AAG, AAT, ACG, ACT, AGG, AGT, ATG, and ATT, which encode Lys, Asn, Thr, Thr, Arg, Ser, Met, and Ile, respectively. Two codons for Thr are present, but the molar sum of these codons is essentially equivalent to any other single codon, due to the decreased concentration of C in the synthetic mixture.

To the fourth subamount (molar ratio 5) is coupled G; next is coupled a mixture of A, C, G, and T in an effective molar ratio of 2:1:1:1, respectively; next is coupled a substantially equimolar mixture of G and T. This provides eight codons: GAG, GAT, GCG, GCT, GGG, GGT, GTG, and GTT, encoding Glu, Asp, Ala, Ala, Gly, Gly, Val, and Val, respectively. Again, even though Ala, Gly and Val are each specified by two codons, the relative concentrations are adjusted so that the codon of each amino acid occurs in substantially equal concentrations.

Thus, this scheme provides codons encoding all twenty amino acids and the stop codon (amber) in substantially equal molar ratios. The synthesis subamounts are combined and mixed, aliquoted into four or five new subamounts, and another mixture of codons is synthesized according to one of the schemes of the invention (one need not use the same scheme each time). This cycle is repeated for each codon in the oligonucleotide desired. A stop codon is generally not desirable where the polynucleotides are to be incorporated into a bacteriophage or plasmid vector for expression in bacteria (e.g., non-suppressor strains which terminate transcription at a TAG codon). However, the polynucleotide library may also be translated in vivo or in vitro in systems having a corresponding amber tRNA charged with a desired modified or unnatural amino acid.

Note that the third step in the cycle for each pool consists of coupling a balanced mixture of G and T. Thus, the four pools may be combined prior to the third step of the cycle, and the G and T coupling conducted simultaneously.

SCHEME 2

The support is divided into four subamounts in a molar ratio of 8:6:3:3. To the first subamount (molar ratio 8) is coupled a substantially equimolar mixture of A and T; followed by coupling to a substantially equimolar mixture of G and T; followed by coupling to a substantially equimolar mixture of G and T. This provides eight codons: AGG, AGT, ATG, ATT, TGG, TGT, TTG, and TTT, encoding Arg, Ser, Met, Ile, Trp, Cys, Leu, and Phe, respectively, in substantially equimolar amounts.

To the second subamount (molar ratio 6) is coupled a substantially equimolar mixture of A, C, and G; followed by coupling to a substantially equimolar mixture of A and C; followed by G alone. This provides six codons: AAG, ACG, CAG, CCG, GAG, and GCG, encoding Lys, Thr, Gln, Pro, Glu, and Ala, respectively.

To the third subamount (molar ratio 3) is coupled a substantially equimolar mixture of A, C, and T; followed by coupling to A; followed by coupling to T. This results in three codons: AAT, CAT, and TAT, encoding Asn, His, and Tyr, respectively, in substantially equimolar amounts.

To the fourth subamount (molar ratio 3) is coupled G; followed by a substantially equimolar mixture of A, G, and T; followed by coupling to T. This provides three codons: GAT, GGT, and GTT, encoding Asp, Gly, and Val, respectively. The third and fourth subamounts couple T in last position of the codon, and thus may be combined for the coupling of T in the last step of each codon generation.

SCHEME 3

The support is divided into four subamounts in an effective molar ratio of 8:4:4:4. To the first subamount (molar ratio 8) is coupled a substantially equimolar mixture of A and T; followed by coupling a substantially equimolar mixture of G and T; followed by coupling another substantially equimolar mixture of G and T. This produces eight codons as with the first subamount in Scheme 2: AGG, AGT, ATG, ATT, TGG, TGT, TTG, and TTT, encoding Arg, Ser, Met, Ile, Trp, Cys, Leu, and Phe, respectively, in substantially equimolar amounts.

To the second subamount (molar ratio 4) is coupled a substantially equimolar mixture of A, C, G, and T; followed by coupling of A; followed by coupling of T. This provides four codons: AAT, CAT, GAT, and TAT, encoding Asn, His, Asp, and Tyr, respectively in substantially equimolar amounts.

To the third subamount (molar ratio 4) is coupled G; followed by a substantially equimolar mixture of A, C, G, and T; followed by coupling of G. This provides four codons: GAG, GCG, GGG, and GTG, encoding Glu, Ala, Gly, and Val, respectively, in substantially equimolar amounts.

To the fourth subamount (molar ratio 4) is coupled a substantially equimolar mixture of A and C; followed by a second substantially equimolar mixture of A and C; followed by coupling to G. This provides four codons: AAG, ACG, CAG, and CCG, encoding Lys, Thr, Gln, and Pro, respectively, in substantially equimolar amounts. The four pools are then recombined to provide and oligonucleotide encoding equal amounts of each of the twenty naturally occurring amino acids.

SCHEME 4

The support is divided into five substantially equimolar subamounts. To the first subamount is coupled a substantially equimolar mixture of A, C, G, and T; followed by coupling of A; followed by coupling of T. This provides four codons: AAT, CAT, GAT, and TAT, encoding Asn, His, Asp, and Tyr, respectively.

To the second subamount is coupled a substantially equimolar mixture of G and C; followed by a substantially equimolar mixture of C and A; followed by G. This results in the synthesis of codons GCG, GAG, CCG, and CAG, encoding Ala, Glu, Pro, and Gln, respectively.

To the third subamount is coupled A; followed by a substantially equimolar mixture of A, C, G, and T; followed by coupling of G. This results in synthesis of the codons AAG, ACG, AGG, and ATG, encoding Lys, Thr, Arg, and Met, respectively. Note that the second and third subamounts may be combined for addition of the terminal G.

To the fourth subamount is coupled a substantially equimolar mixture of A and T; followed by a substantially equimolar mixture of G and T; followed by coupling of T. This results in the codons AGT, ATT, TGT, and TTT, encoding Ser, Ile, Cys, and Phe, respectively. Note that the first and fourth pools may be combined for addition of the terminal T.

To the fifth subamount is coupled a substantially equimolar mixture of G and T; followed by a second substantially equimolar mixture of G and T; followed by coupling of G. This results in the codons GGG, GTG, TGG, and TTG, encoding Gly, Val, Trp, and Leu, respectively.

SCHEME 5

The support is divided into five equal subamounts. To the first subamount is coupled a substantially equimolar mixture of A, C, G, and T; followed by coupling of A; followed by coupling of T. This provides four codons: AAT, CAT, GAT, and TAT, encoding Asn, His, Asp, and Tyr, respectively.

To the second subamount is coupled a substantially equimolar mixture of G and C; followed by a substantially equimolar mixture of C and A; followed by coupling of G. This results in the codons GCG, GAG, CCG, and CAG, encoding Ala, Glu, Pro, and Gln, respectively.

To the third subamount is coupled A; followed by a substantially equimolar mixture of A, C, G, and T; followed by coupling of G. This results in the codons AAG, ACG, AGG, and ATG, encoding Lys, Thr, Arg, and Met, respectively.

To the fourth subamount is coupled a substantially equimolar mixture of C and G; followed by a second substantially equimolar mixture of C and A; followed by coupling of G. This provides the codons CCG, CAG, GCG, and GAG, encoding Pro, Gln, Ala, and Glu, respectively. Note that the second and fourth subamounts may be combined for addition of the substantially equimolar mixture of C an A, and that the second, third, and fourth subamounts may be combined for addition of the terminal G.

To the fifth subamount is coupled T; followed by a substantially equimolar mixture of G and T; followed by a second substantially equimolar mixture of G and T. This provides the codons TGG, TGT, TTG, and TTT, encoding Trp, Cys, Leu, and Phe, respectively.

The five subamounts are then combined and mixed, providing a combined amount of supports having substantially equimolar amounts of codons for each amino acid.

Example of Scheme 1:

A resin suitable for the synthesis of nucleotide sequences is divided into four parts in the ratio of 6:3:7:5 where the synthesis of a "random" amino acid is required.

Thymine is attached to the first portion of resin (comprising 6/21 of the total resin) as the first base of the codon by reacting the resin with an activated solution of thymine. After coupling, the resin is reacted with a mixture of activated nucleotides such that adenine, guanine and thymine are coupled with equal efficiency in the second position of the codon (i.e., from a mixture of A, T, and G in substantially equimolar amounts). Finally, the resin is reacted with a mixture of thymine and guanine such that substantially equal amounts of the bases are coupled at the last position of the codon (i.e., from a mixture of G and T in substantially equimolar amounts). Note that the mixture for the 3rd base of the codon can be replaced by a mixture of cytosine and guanine such that equal amounts of the bases will be coupled (i.e., from a substantially equimolar mixture of C and G rather than a substantially equimolar mixture of T and G). Thus, this portion of the resin (subamount having molar ratio 6) will have the following codons synthesized:

| Codon | Molar Ratio | Amino acid |
|---|---|---|
| TAT | 1.00 | Tyr |
| TAG | 1.00 | Stop codon |
| TGT | 1.00 | Cys |
| TGG | 1.00 | Trp |
| TTT | 1.00 | Phe |
| TTG | 1.00 | Leu |

In this table, each molar ratio refers to the amount of codon on 1/21 of the total resin. Thus, this portion of the resin has equal numbers of codons encoding five amino acids plus the Stop codon.

The second portion of the resin (comprising 3/21 of the total resin) is reacted so that a cytosine is coupled at the first position of the codon. After processing, the resin is reacted with an activated mixture of the bases cytosine and adenine. However, the relative concentrations of the A and C are adjusted so that two moles of adenine are coupled for each mole of cytosine. Finally, the resin is reacted with a mixture of thymine and guanine in substantially equimolar amounts that gives equal coupling of both bases at the last position of the codon. Thus, the four possible codons synthesized on this portion of the resin are:

| Codon | Molar ratio | Amino acid |
|---|---|---|
| CAT | 1.00 | His |
| CAG | 1.00 | Gln |
| CCT | 0.50 | Pro |
| CCG | 0.50 | Pro |

Thus, this portion of the resin contains four codons, but the codons encode three amino acids in equal amounts.

The third portion of the resin, comprising 7/21 of the total resin, couples adenine in the first position of the codon. Next this portion of the resin is reacted with a mixture of the bases adenine, cytosine, thymine and guanine, adjusting the concentration of the bases such that two moles each of adenine, guanine and thymine are coupled for each mole of cytosine. Finally, this portion of the resin is reacted with a substantially equimolar mixture of guanine and thymine that provides equal coupling of both bases. Thus, on the resin in this subamount, 8 different codons are synthesized, at known but unequal molar ratios. They are:

| Codon | Molar ratio | Amino acid |
|---|---|---|
| AAT | 1.00 | Asn |
| AAG | 1.00 | Lys |
| ACT | 0.50 | Thr |
| ACG | 0.50 | Thr |
| AGT | 1.00 | Ser |
| AGG | 1.00 | Arg |
| ATT | 1.00 | Ile |
| ATG | 1.00 | Met |

Thus, eight codons are synthesized coding for seven amino acids in substantially equal molar ratios.

The last pool of the resin (5/21 of the total resin) has guanine coupled in the first position of the codon. The second base of the codon is coupled from a mixture of all four bases such that two moles of adenine are coupled for each mole of cytosine, guanine and thymine (i.e. a mixture of A, C, G, and T in an effective molar ratio of 2:1:1:1). Finally, the third base of the codon is coupled from a substantially equimolar mixture of thymine and guanine such that equal numbers of both bases are coupled in this position. Thus, in this pool of resin particles, 8 different codons synthesized:

| Codon | Molar ratio | Amino acid |
|---|---|---|
| GAT | 1.00 | Asp |
| GAG | 1.00 | Glu |
| GCT | 0.50 | Ala |
| GCG | 0.50 | Ala |
| GGT | 0.50 | Gly |
| GGG | 0.50 | Gly |
| GTT | 0.50 | Val |
| GTG | 0.50 | Val |

Thus, the eight codons are synthesized on this portion of the resin encode five amino acids in substantially equal molar ratios.

After the codons have been synthesized the resin pools (subamounts) are recombined. It should be noted in this example that the step of coupling the third base of the codon is identical for each subamount. Thus, the resin may been pooled after coupling the second base of the codon, allowing the bases in the third position to be coupled in a single step. Such a variation is to be considered within the ambit of this invention.

Thus, every amino acid has at least one codon synthesized for it. Furthermore, the sum of the molar ratios of codons synthesized for each amino acid are substantially equal.

It will be apparent to those of ordinary skill in the art that different combinations of subamounts of resin and combinations of reactive bases will yield the same result as the example above. Such variations are to be regarded as within the ambit of this invention.

The practical advantage of this embodiment of the invention is that it becomes possible to synthesize the codons of longer "random" peptides. Consider the case where every possible polynucleotide encoding a hexapeptide is synthesized. Division of the resin into 20 separate subamounts and generation of a codon for each amino acid separately implies that there will be $6.4 \times 10^7$ ($=20^6$) different combinations of codons for a polynucleotide encoding a hexapeptide. Thus, the theoretical minimum number of resin particles required to synthesize a hexapeptide is the number of resin particles that can be divided into twenty subamounts six times, or $6.4 \times 10^7$. In the first example of the invention given above, the smallest division of the resin particles occurs where the resin is divided into 3/21 (=1/7) of the total resin. Therefore, the theoretical minimum number of resin particles required to synthesize the polynucleotides for all hexapeptides is the number of resin particles that can be apportioned into sevenths six times, or 117,649 (=$7^6$). Since each resin particle can have coupled to it 500 or more polynucleotides, the reduced number of resin particles does not limit the number of possible different polynucleotide sequences that can be synthesized. It will be understood by one of ordinary skill in the art that as the length of the desired polynucleotide increases, a predictable increase in the amount of resin is needed to have a sufficient amount of each species.

The reduction in the minimum number of resin particles has important practical consequences. Consider the case where the minimum number of resin particles is $6.4 \times 10^7$. Suppose, further, that there will be an average of 10 particles per polynucleotide encoding a hexapeptide. This implies that there will be $6.4 \times 10^8$ resin particles. Resins suitable for polynucleotide syntheses typically have about $0.5 \times 10^6$ particles/mL. Thus, 1.28 liters of resin will be required. This is a prodigious amount of resin, and very expensive. Commercial nucleotide synthesizers typically operate with 1 to 10 mL of resin. There is, however, a fundamental weakness in only having 10 resin particles per polynucleotide encoding a hexapeptide. There is a small, but finite, probability that there will be no resin particle for a particular polynucleotide encoding a hexapeptide. Assuming that the distribution of resin particles follows an expected Poisson distribution, and that there are 10 particles per polynucleotide encoded, the probability that there will be no resin particle for a particular polynucleotide encoding a hexapeptide is $4.54 \times 10^{-5}$ (=$e^{-10}$), i.e., 1 in 22,026. A practitioner of ordinary skill in the art could expect about 3000 (=$6.4 \times 10^7/22,026$) polynucleotides encoding a hexapeptide to be missing from the synthesis. If 20 resin particles per polynucleotide were used, the probability reduces to $2.06 \times 10^{-9}$ i.e., 1 in $4.9 \times 10^8$.

Providing twenty particles per polynucleotide encoding a hexapeptide provides a higher probability that all polynucleotides encoding a hexapeptide are made. However, the Poisson distribution of the number of particles per polynucleotide encoding a peptide is uneven. Increasing the average number of resin particles to approximately 100 particles per polynucleotide encoding a peptide provides an acceptable distribution of numbers of resin particles per given polynucleotide.

Reduction of the minimum number of resin particles by the method of the invention to 117,649 as demonstrated in this Example, means that 100 times this number will fit into a volume of 23.5 Ml. This is a practical volume to use in a synthesis.

Example of Scheme 2:

Example 1 will produce all the codons for each amino acid so that the amino acids are represented equally and includes the TAG stop codon. This example of the invention provides a method of generating random codons in which stop codons are not synthesized.

In this example the resin is divided into 4 pools in the ratio 8:6:3:3. In this and following examples, if a mixture of bases is used in the coupling step, the molar ratio of each base is adjusted so that substantially equal numbers of each base are coupled to the lengthening nucleotide.

The largest portion of the resin, comprising 8/20 of the total resin, is reacted with A and T at the first position of the codon. In the second position of the codon the resin is reacted with G and T. To couple the last base of the codon, the resin is reacted again with G and T. Thus, on this subamount of resin, eight codons will be synthesized in substantially equal amounts and code for eight amino acids:

| Codon | Molar ratio | Amino acid |
|-------|-------------|------------|
| AGG   | 1.00        | Arg        |
| AGT   | 1.00        | Ser        |
| ATG   | 1.00        | Met        |
| ATT   | 1.00        | Ile        |
| TGG   | 1.00        | Trp        |
| TGT   | 1.00        | Cys        |
| TTG   | 1.00        | Leu        |
| TTT   | 1.00        | Phe        |

In this and following lists provided herein, the column heading, "Molar ratio" refers to the amount of each codon on 1/20 of the total resin.

The second subamount of resin, comprising 6/20 of the total resin, is reacted with the substantially equimolar mixture of A, C, and G to couple a base in the first position of the codon. A substantially equimolar mixture of A and C is used to couple a base in the second position of the codon. The final base coupled to this subamount of resin is guanine. Thus, six different codons will be synthesized on this subamount of resin, each coding for a different amino acid:

| Codon | Molar ratio | Amino acid |
|-------|-------------|------------|
| AAG   | 1.00        | Lys        |
| ACG   | 1.00        | Thr        |
| CAG   | 1.00        | Gln        |
| CCG   | 1.00        | Pro        |
| GAG   | 1.00        | Glu        |
| GCG   | 1.00        | Ala        |

The third subamount of resin, comprising 3/20 of the total resin, has the base in the first position coupled from the substantially equimolar mixture A, C, and T. Adenine is coupled in the second position and thymine is coupled in the third position of the codons. Thus, three codons are synthesized, each coding for a different amino acid:

| Codon | Molar ratio | Amino acid |
|-------|-------------|------------|
| AAT   | 1.00        | Asn        |
| CAT   | 1.00        | His        |
| TAT   | 1.00        | Tyr        |

The final fourth subamount of resin, comprising 3/20 of the total resin, couples guanine as the base in the first position of the codon. The second base of the codon is coupled from a substantially equimolar mixture A, G, and T, and the last base in the codons is thymine. This gives three codons synthesized on this resin subamount:

| Codon | Molar ratio | Amino acid |
|-------|-------------|------------|
| GAT   | 1.00        | Asp        |
| GGT   | 1.00        | Gly        |
| GTT   | 1.00        | Val        |

When a codon has been synthesized on each resin subamount, the subamounts are recombined. In this way, each amino acid is encoded in substantially equal molar ratios. Also Scheme 2 and Example 2 provide a method of the invention in which no stop codon is generated. This procedure is repeated a sufficient number of times to generate codons for all possible peptides of a desired length.

As the smallest pool of resin is 3/20 of the total, the theoretical minimum number of resin particles needed to synthesize codons for all hexapeptides will be 87,791 (=(20/3)$^6$). One hundred times this amount is preferably used in practicing the invention.

It will be appreciated that variations of the procedure are possible. For instance, the largest subamount, representing 8/20 of the total resin, could be divided into two substantially equal portions. One of these can have thymine coupled in the first base position of the codon, and the other can have guanine coupled in the first base position. The second and third bases of the codons can then be generated as described above. Such variations are regarded as within the ambit of this invention.

It will also be obvious to those of ordinary skill in the art that thymine in the third base position of each codon can be replaced with cytosine. This will change the codons present on the resin without changing the amino acid that will be translated. For instance, in Example 2 above, in the final subamount the last base coupled can be cytosine. In this case, the following codons will be synthesized:

| Codon | Molar ratio | Amino acid |
|-------|-------------|------------|
| GAC   | 1.00        | Asp        |
| GGC   | 1.00        | Gly        |
| GTC   | 1.00        | Val        |

Thus, the codons have changed but the encoded amino acids are unaltered due to the degeneracy of the genetic code. Such variations of the method are intended to be within the ambit of the invention.

Example of Scheme 3:

A preferred embodiment of the invention reduces the theoretical minimum number of resin particles to 15,625. This is achieved by dividing the resin into 4 pools in the ratio 8:4:4:4. In this case the theoretical minimum number of resin particles is the number of particles that can be divided into 4/20 portions (the smallest portion) six times using a hexapeptide as an example, or 5$^6$ (=15,625).

The largest pool, comprising of 8/20 of the total resin has the base in the first position of the codon coupled from a substantially equimolar mixture of A and T; the second base from a substantially equimolar mixture of G and T; and the last base from a substantially equimolar mixture of G and T. Thus, eight codons are generated for 8 different amino acids. These are:

| Codon | Molar ratio | Amino acid |
|-------|-------------|------------|
| AGG   | 1.00        | Arg        |
| AGT   | 1.00        | Ser        |
| ATG   | 1.00        | Met        |
| ATT   | 1.00        | Ile        |
| TGG   | 1.00        | Trp        |
| TGT   | 1.00        | Cys        |
| TTG   | 1.00        | Leu        |
| TTT   | 1.00        | Phe        |

The next subamount, comprising of 4/20 of the total resin, has the first base coupled from a substantially equimolar mixture of A, C, G, and T; the second and third bases of the codons are adenine and thymine, respectively. This gives four codons generated:

| Codon | Molar ratio | Amino acid |
|-------|-------------|------------|
| AAT   | 1.00        | Asn        |
| CAT   | 1.00        | His        |
| GAT   | 1.00        | Asp        |
| TAT   | 1.00        | Tyr        |

The next subamount of resin, comprising 4/20 of the total resin, has guanine as the first base; the second base is coupled from a substantially equimolar mixture of A, C, G, and T; and the third base is guanine. This gives four codons generated:

| Codon | Molar ratio | Amino acid |
|-------|-------------|------------|
| GAG   | 1.00        | Glu        |
| GCG   | 1.00        | Ala        |
| GGG   | 1.00        | Gly        |
| GTG   | 1.00        | Val        |

The last subamount of resin, again comprising 4/20 of the total resin, has its first two bases coupled in separate reactions from a substantially equimolar mixture of A and C; and the third base is guanine. This gives four codons generated:

| Codon | Molar ratio | Amino acid |
|-------|-------------|------------|
| AAG   | 1.00        | Lys        |
| ACG   | 1.00        | Thr        |
| CAG   | 1.00        | Gln        |
| CCG   | 1.00        | Pro        |

After the codons are synthesized, the subamounts are recombined. The procedure is repeated five more times to generate polynucleotide sequences that code for all possible hexapeptide sequences in substantially equal molar ratios.

Because the smallest subamount of resin is now 4/20 of the total, the theoretical minimum number of resin particles required is 15,625 (=5$^6$) Thus, a 100 fold excess of resin would be contained in about 3.1 mL.

It should be apparent that variations of this example exist as described in Example 2. Again, such variations are included within the ambit of the invention.

Two other schemes of dividing the resin into subamounts and reacting with mixtures of bases yield codons for all amino acids in substantially equal molar ratios and no stop codon. Both divide the resin pool into five substantially equal portions. Both have three of the resin subamounts treated in the same manner:

The first subamount has its first base coupled from a substantially equimolar mixture A, C, C, and T; and the second and third bases are adenine and thymine, respectively. The second subamount has the first base coupled from a substantially equimolar mixture C and G; the second base is coupled from a substantially equimolar mixture of C and A; and the last base is guanine. The third subamount has adenine as the first base; the second base is coupled from a substantially equimolar mixture of A, C, G, T; and the last base is guanine.

In one method, the fourth subamount has its first base coupled from a substantially equimolar mixture of A and T; the second base from a substantially equimolar mixture of G and T; and the third base is thymine. The fifth pool of resin has the first and second base coupled from a substantially equimolar mixture of G and T; and the last base is guanine.

In another method, the fourth resin subamount has its first base coupled from a substantially equimolar mixture of C and G; its second base coupled from a substantially equimolar mixture C and A; and its last base is guanine. The fifth pool has thymine as the first base; and the second and third bases are coupled from a substantially equimolar mixture of G and T.

Each of these alternatives requires the same theoretical minimum number of resin particles (15,625) for the synthesis of a hexapeptide, as in this example. Note, any of the three alternatives given in this example can be used to provide a particular amino acid codon in generating the sequence for a "random" polypeptide.

To be useful in genetic manipulations, the restriction endonuclease chosen to cleave a polynucleotide encoding a peptide in preparation for cloning must not cleave the synthetic DNA. This is easily checked since the sequence is known for every possible polynucleotide synthesized. For example, consider the restriction endonuclease AatII from *Acetobacter aceti*. This enzyme recognizes the sequence 5'-GACGTC-3'. Consider the codons of the amino acids as described in Example 3 above. That is:

| Amino acid | | CODON |
|---|---|---|
| Ala | Alanine | GCG |
| Asn | Asparagine | AAT |
| Asp | Aspartic acid | GAT |
| Arg | Arginine | AGG |
| Cys | Cysteine | TGT |
| Gln | Glutamine | CAG |
| Glu | Glutamic acid | GAG |
| Gly | Glycine | GGG |
| His | Histidine | CAT |
| Ile | Isoleucine | ATT |
| Leu | Leucine | TTG |
| Lys | Lysine | AAG |
| Met | Methionine | ATG |
| Phe | Phenylalanine | TTT |
| Pro | Proline | CCG |
| Ser | Serine | AGT |
| Thr | Threonine | ACG |
| Trp | Tryptophan | TGG |
| Tyr | Tyrosine | TAT |
| Val | Valine | GTG |

The recognition sequence must be checked for codons in each frameshift position. Thus, in the unshifted position (i.e., GAC-GTC) the enzyme will attack none of the codons as they do not exist in this set. In the first frameshift position (i.e., considering the recognition sequence as G-ACG-TC) there are 10 codons that have G in the third position, and threonine is coded by ACG. However, no codon starts with TC and therefore, with a frameshift of 1 base the hexapeptide codon will not be cleaved with this enzyme. Finally with a frameshift of 2 bases (i.e., considering the sequence GA-CGT-C), the triplet CGT is absent from the set. Therefore, the enzyme Aat II is suitable for use with this set of codons as no combination will lead to the recognition sequence.

In another case, the enzyme AccI from *Acinetobacter calcoaceticus*, which has the recognition sequence 5'-GT(A, C)(G,T)AC-3' would be unsuitable for use with polynucleotides encoding peptide made from these codons. Multiple combinations of these codons will yield the AccI recognition sequence. One example is Ala-Tyr-Thr which has the code GCGTATACG. It was found that 28 out of 50 commercially available restriction endonucleases (having different recognition sequences), were compatible with the set of codons used in this example. That is, no combination of the codons yielded the recognition sequence of these 28 enzymes.

Each of the schemes and examples set forth above results in support mixtures having a number of different polynucleotide sequences. Each combined support mixture has a plurality of sequences with each codon position represented by each amino acid in a substantially equimolar ratio. The methods of the invention reduce the number of support particles required to generate a polynucleotide library of substantial diversity (i.e., having a large number of diverse sequences).

Following recombination of the divided pools, an additional sequence may be added to the codons. The mixture may be again divided according to one of the Schemes, and a second mixture of codons synthesized, or one may add a common sequence to the entire mixture, or a combination thereof. When the complete polynucleotide library has been synthesized, it may be cleaved from the support by the use of cleavable linkages to the support. The free oligonucleotides may then be converted to double-stranded DNA and cloned into a vector or phage for use in a biopanning assay as described by J. Devlin et al. (*Science* (1990) 249:404–406). Alternatively, one may amplify the polynucleotides and translate them in a cell free system, for example as described by Kawasaki (WO91/05058) or Gold et al. (WO92/02536).

Isolation of full-length polynucleotides can be aided by coupling of a selectable nucleotide sequence to the polynucleotide. The selectable nucleotide sequence can be coupled to the activated resin prior to synthesis of the random codons; or the selectable nucleotide sequence can be coupled to the polynucleotide following completion of the random codon-containing polynucleotide of interest.

The method of the present invention can be carried out by varying the molar ratios of the subamounts of resin as well as the molar ratios and/or concentrations of the activated nucleotide residues in a particular mixture. This provides substantially equal representation of each amino acid at a given codon of a synthesized mixture of random polynucleotides.

Selection

As described above, the method of the invention results in a complex mixture of polynucleotides. Although the mixture is likely to be complex and contain a large number of different polynucleotides it will have a known composition in that (i) each coupling reaction is driven to completion; (ii) the reactants i.e., the resin and the activated nucleotide or activated nucleotides reacted in each coupling step in each subamount are known; (iii) the amount of each codon produced in each coupling iteration is known; and (iv) the amount of each polynucleotide added in the recombining step is known. Although the composition is known, only one or a few of the polynucleotides in the mixture are polynucleotides encoding a desired peptide having a target biological property. Accordingly, it is necessary to select from the mixture those products which encode a peptide of the desired properties.

The selection process can begin with conversion of the single stranded polynucleotides to double stranded polynucleotides in preparation for cloning. In the case of polydeoxynucleotide synthesis, a complementary strand can be produced by DNA polymerase priming synthesis from a primer complementary to a known oligonucleotide coupled to the random polynucleotide. Following second strand synthesis, the double stranded DNA encoding a random peptide can be cut at predetermined restriction sites that have been incorporated into the polynucleotide during synthesis. As described above, the choice of restriction enzyme is dependent on the sequences of the polynucleotides synthesized. Since the sequences are known, one of ordinary skill in the art can select an enzyme that cuts only at the restriction sites outside of the coding region for the random peptide. The cleaved fragments are next cloned into an expression vector and introduced into a host organism (such as a bacterium) for amplification of the DNA and expression of the random peptide.

The expressed peptide can be detected by incorporation of a labeled amino acid (such as a radiolabeled amino acid, $^{35}$S-Met, for example) into a specific codon outside of the polynucleotide nucleotide sequence encoding a random peptide for testing. The expression vector chosen for this purpose is one which preferentially expresses the cloned insert (e.g., the RNA polymerase of bacteriophage T7 expresses from promoters that are rarely encountered in DNA unrelated to T7 DNA).

An initial screening can be performed on clonal populations of each cell into which a random polynucleotide-containing vector is introduced. Large numbers of clonal populations can be screened simultaneously by pooling populations prior to screening. The known members of a pool providing a positive result in a particular screen are repooled in smaller groups and the screen repeated until the clonal population producing the peptide having the target property is identified.

The nature of the process for selecting a peptide having the desired target property depends, of course, on the nature of the product for which selection is to be had. In a common instance, wherein the desired property is the ability to bind a protein such as an immunoglobulin, receptor, receptor-binding ligand, antigen or enzyme, selection can be conducted simply by exposing to the substance to which binding is desired a cell lysate or pool of cell lysates each containing a random peptide. The desired peptides will bind preferentially. (Other nonprotein substances, such as carbohydrates or nucleic acids, could also be used.) The bound substances are then separated from the remainder of the mixture (for example, by using the binding substance conjugated to a solid support and separating using chromatographic techniques or by filtration or centrifugation, or separating bound and unbound peptides on the basis of size using gel filtration). The bound peptides can then be removed by denaturation of the complex, or by competition with the naturally occurring substrate which normally binds to the receptor or antibody.

This general method is also applicable to proteins responsible for gene regulation as these peptides bind specifically to certain DNA sequences.

Other properties upon which separation can be based include selective membrane transport, size separation based on differential behavior due to 3-dimensional conformation (folding) and differences in other physical properties such as solubility or freezing point.

If very large subpopulations of polynucleotides cloned into expression vectors are obtained, reapplication of the selection technique at higher stringency may be needed. Selection can be conducted on individual components, or on mixtures having limited numbers of components. Thus, for example, if a mixture of peptides binding to a given antibody or receptor contains fifty or so members, the salt concentration of Ph can be adjusted to dissociate all but the most tightly binding members, or the natural substrate can be used to provide competition. This refinement will result in the recovery of a mixture with a more manageable number of components. A variety of protocols will be evident to differentiate among peptides with varying levels of the target characteristics.

Analysis

When individual peptides have been obtained, the clonal population expressing each peptide is traced, vector DNA is isolated and the DNA sequence of the insert encoding the peptide is sequenced by methods well known in the art. Producing a random peptide using the method of the invention provides the advantage of exploiting DNA sequencing methods rather than more difficult amino acid sequencing methods to determine the deduced amino acid sequence of the biologically active peptides. Since the polynucleotide sequence encoding the active peptide is naturally amplified in the expressing host, the amount of DNA available is sufficient for accurate sequencing of the insert DNA by standard techniques.

Standard methods of analysis can be used to obtain the amino acid sequence information needed to specify the particular peptide recovered if desired. These methods include determination of amino acid composition, including the use of highly sensitive methods such as fast atom bombardment mass spectrometry (FABMS) which provides the very precise molecular weight of the peptide components of a mixture such as when peptides are expressed in vitro from a mixture of polyribonucleotides synthesized by the method of the invention. Sequence information of peptides expressed in vivo can be obtained by a variety of methods well known to those of ordinary skill in the art.

The mixture of polynucleotides synthesized by the method of the invention can be made double stranded and cloned into an expression vector such that a fusion protein is produced by expression of the polynucleotides of the mixture. Such cloning is well known to those of ordinary skill in the art and is useful, for example, by exploiting the properties of the fused protein such as to mark the expressed peptide of the mixture.

The method of the invention allows an active peptide to be produced in large amounts for further sequence analysis, or further biological testing without having to design and clone a protein expression system after identifying an active peptide. Using the method of the invention, the active peptide can be quickly overexpressed and analyzed further to confirm its activity or to characterize its other properties.

SUMMARY

Controlled synthesis of a mixture of polynucleotides having a known composition and encoding one or more peptides of having a desired target property is disclosed. The method provides that each amino acid is substantially equally encoded by the codons synthesized in each synthetic cycle. The method involves five essential steps. First, a given amount of prepared resin (or a mixture of resins) is divided into a number of subamounts with each subamount preferably containing a known molar ratio of resin. Next, a first single activated nucleotide or a mixture of activated nucleotides are coupled to the resin in each of the subamounts and the coupling reaction is driven to completion. In a next step, a second activated nucleotide (or mixture) is coupled to the first nucleotide and the coupling reaction is driven to completion. In a next step, a third activated nucleotide (or mixture) is coupled to the second nucleotide and the coupling reaction is again driven to completion. Next, the subamounts of resin are combined, after which the newly created codons in known molar ratios encode all of the amino acids in substantially equimolar amounts. The steps can be repeated to lengthen the polynucleotide chain and chains can be linked. Thereafter, methods can be employed to detect the desired polynucleotide in the mixture, clone and express it, and carry out analyses such as the determination of the nucleic acid sequence, the deduced amino acid sequence, or the amino acid sequence itself following overproduction of the desired peptide.

This invention provides a simple method of preparation of complex mixtures of polynucleotides where codon synthesis is performed to overcome the bias of the degenerate genetic code and allow each amino acid to be substantially equally encoded at a given codon position. Because the mixture will contain detectable amounts of polynucleotides, cloning, expression, and selection of those members encoding peptides with the desired target properties is possible. Examples of target properties include binding to various moieties including proteins, such as enzymes, receptors, receptor-binding ligands or antibodies, nucleic acids, and carbohydrates, reaction with enzymes to form distinct products, or other properties such as transport through membranes, anti-freeze properties, and as vaccines.

The method of the invention offers the opportunity to maximize the desired property by selection of the most active peptide expressed by a mixture of polynucleotides in which each codon position is randomized as to the amino acid it encodes. The inherent statistical bias at each codon position for amino acids encoded by multiple codons according to the degeneracy of the genetic code is overcome by the method of the invention as is the ability to avoid encoding a stop codon in a random codon sequence.

While the present invention has been described with reference to the specific embodiments thereof, it should be understood by those of ordinary skill in the art of synthesizing polynucleotides that various changes may be made and equivalents may be substituted without departing from the true spirit and scope of the present method for making polynucleotide mixtures and isolating desired peptides from the expressed polynucleotides. In addition, many modifications may be made to adapt to a particular situation, material, composition of matter, process, process step or steps, to the objective, spirit and scope of the present invention. All such modifications are intended to be within the scope of the appended claims.

What is claimed is:

1. A method of preparing on a number of support resin particles a mixture of polynucleotides having different nucleotide codon sequences encoding the twenty naturally occurring amino acids in substantially equimolar amounts, said method comprising:
   a) dividing a number of prepared support resin particles into a group consisting of four or five subamounts of known proportions;
   b) coupling to a first subamount of step (a) a first activated nucleotide from a mixture of least one activated nucleotide, wherein said nucleotide in said mixture is present in a known proportion, wherein a plurality of different resin-nucleotide reaction products are obtained, wherein said coupling is carried out under conditions such that said coupling is driven to substantial completion, and wherein the 3' reactive site of said resin-nucleotide is deprotected following said coupling;
   c) coupling to the first subamount of step (a) a second activated nucleotide from a mixture of at least one activated nucleotide, wherein each of said activated nucleotides is present in said mixture in a known proportion, wherein a plurality of resin-nucleotide reaction products are obtained, wherein said coupling is carried out under conditions that drive said coupling to substantial completion, and wherein the 3' reactive site of said resin-nucleotide is deprotected following said coupling;
   d) coupling to the first subamount of step (a) a third activated nucleotide from a mixture of at least one activated nucleotide, wherein each of said activated nucleotides is present in said mixture in a known proportion, wherein a plurality of resin-nucleotide reaction products are obtained, wherein said coupling is carried out under conditions that drive said coupling to substantial completion, and wherein the 3' reactive site of said resin-nucleotide is deprotected following said coupling;
   e) repeating steps (b), (c), and (d) in a manner such that different nucleotide sequences are synthesized on a plurality of additional subamounts of step (a) to obtain a plurality of reaction products on support resin, wherein each polynucleotide is present in a detectable, retrievable, and clonable amount, wherein the reaction products comprise a plurality of sequences at a codon position in amounts such that expression of the sequences results in equimolar amounts of the twenty amino acids at the codon position, and wherein the number of codons at each codon position exceeds the number of encoded amino acids.

2. The method of claim 1, wherein the number of prepared support resin particles in step (a) comprises 100 times the minimum number of particles that can be divided by the smallest subamount as many times as there are repetitions of steps (a) through (e).

3. The method according to claim 1, wherein said number of prepared support resin particles is divided in step (a) into four subamounts.

4. The method according to claim 1, wherein said number of prepared support resin particles is divided in step (a) into five subamounts.

5. The method of claim 1, wherein said prepared support has covalently attached to it at least one polynucleotide sequence.

6. The method of claim 3, wherein said dividing results in subamounts having the effective molar ratio of 6:3:7:5.

7. The method of claim 3, wherein:
   a) said dividing results in subamounts having the effective molar ratio of 6:3:7:5; and
   b) said combining step occurs prior to said coupling of said third activated nucleotide wherein said third activated nucleotide is the same for each subamount.

8. The method of preparing a mixture of polynucleotides as claimed in claim 1, further comprising detecting at least one polynucleotide in the mixture wherein said polynucleotide has a target property.

9. The method of claim 8, wherein said polynucleotide is single stranded RNA.

10. The method of claim 8, wherein said polynucleotide is single stranded DNA.

11. The method of preparing a mixture of polynucleotides as claimed in claim 1, further comprising:
   a) detecting at least one polynucleotide in the mixture;
   b) synthesizing a complementary strand to said polynucleotide;
   c) cloning said polynucleotide into an expression vector;
   d) expressing said cloned polynucleotide in a host organism; and
   e) producing an expression product having a selected target property.

12. The method of claim 11, wherein said expression product is RNA.

29

13. The method of claim 11, wherein said expression product is double stranded DNA.

14. The method of claim 11, wherein said expression product is a peptide.

15. The method of claim 8, further comprising sequencing said polynucleotide.

16. The method of claim 11, further comprising sequencing said cloned polynucleotide.

17. The method of claim 1, wherein said activated nucleotides are activated deoxyribonucleotides.

18. The method of claim 1, wherein said activated nucleotides are activated ribonucleotides.

19. The method of claim 1, wherein each of said activated nucleotides is selected from the group consisting of an activated deoxyribonucleotide and an activated ribonucleotide.

20. The method of claim 1, further comprising:
monitoring a coupling reaction by an analytical method to determine the degree of completion of said coupling.

21. The method of claim 13, wherein said DNA has a target property.

22. The method of claim 12, wherein said RNA has a target property.

23. The method of claim 14, wherein said peptide has a target property.

24. The method of claim 1, wherein the composition of said random mixture of resin-nucleotide reaction products comprises substantially equimolar amounts of each naturally-occurring amino acid encoded at at least one of the codon positions of said resin-polynucleotide products.

25. The method of claim 1, wherein the composition of said random mixture of resin-polynucleotide reaction products is predetermined.

26. The method of claim 1, wherein said mixture of resin-polynucleotide reaction products contains polynucleotides encoding 400 or more different peptides of distinct, unique and different amino acid sequences, wherein the presence of each polynucleotide in the mixture is predetermined, each polynucleotide is present in the mixture in detectable and clonable amounts and the mixture contains at least one polynucleotide encoding a biologically active peptide.

27. The method of claim 1, wherein said mixture of resin-polynucleotide reaction products contains polynucleotides encoding 8,000 or more different peptides of distinct, unique and different amino acid sequences, wherein the presence of each polynucleotide in the mixture is predetermined, each polynucleotide is present in the mixture in detectable and clonable amounts and the mixture contains at least one polynucleotide encoding a biologically active peptide.

28. The method of claim 1, wherein said mixture of resin-polynucleotide reaction products contains polynucleotides encoding 160,000 or more different peptides of distinct, unique and different amino acid sequences, wherein the presence of each polynucleotide in the mixture is predetermined, each polynucleotide is present in the mixture in detectable and clonable amounts and the mixture contains at least one polynucleotide encoding a biologically active peptide.

30

29. The method of claim 1, wherein said mixture of resin-polynucleotide reaction products contains polynucleotides encoding 3,200,000 or more different peptides of distinct, unique and different amino acid sequences, wherein the presence of each polynucleotide in the mixture is predetermined, each polynucleotide is present in the mixture in detectable and clonable amounts and the mixture contains at least one polynucleotide encoding a biologically active peptide.

30. The method of claim 1, wherein said mixture of resin-polynucleotide reaction products contains polynucleotides encoding 64,000,000 or more different peptides of distinct, unique and different amino acid sequences, wherein the presence of each polynucleotide in the mixture is predetermined, each polynucleotide is present in the mixture in detectable and clonable amounts and the mixture contains at least one polynucleotide encoding a biologically active peptide.

31. The method of claim 14, further comprising:
a) expressing said peptide as part of a surface protein present on the surface of a filamentous bacteriophage; and
b) screening said peptide for a target property.

32. The method of claim 1, wherein each particle of said prepared support resin has covalently attached to it at least one polynucleotide sequence.

33. The method of claim 1, wherein the resulting polynucleotide sequences encode an equimolar mixture of peptides.

34. A predetermined mixture of polynucleotides containing 400 or more different polynucleotides each encoding distinct, unique and different amino acid sequences, wherein the presence of each polynucleotide in the mixture is predetermined, each polynucleotide is present in the mixture in detectable and clonable amounts and the mixture includes at least one polynucleotide in a detectable and clonable amount that encodes a biologically active peptide, and wherein the number of different codons exceeds the number of different amino acids encoded by the polynucleotides.

35. A mixture as claimed in claim 34, wherein said mixture contains 8,000 or more different polynucleotides each encoding a peptide of distinct, unique and different amino acid sequences.

36. A mixture as claimed in claim 34, wherein said mixture contains 160,000 or more different polynucleotides each encoding a peptide of distinct, unique and different amino acid sequences.

37. A mixture as claimed in claim 34, wherein said mixture contains 3,200,000 or more different polynucleotides each encoding a peptide of distinct, unique and different amino acid sequences.

38. A mixture as claimed in claim 34, wherein said mixture contains 64,000,000 or more different polynucleotides each encoding a peptide of distinct, unique and different amino acid sequences.

* * * * *